United States Patent
Weng et al.

(10) Patent No.: US 12,252,476 B2
(45) Date of Patent: Mar. 18, 2025

(54) BIO-BASED EPOXY CHAIN EXTENDER AND PREPARATION METHOD THEREOF

(71) Applicant: BEIJING TECHNOLOGY AND BUSINESS UNIVERSITY, Beijing (CN)

(72) Inventors: Yunxuan Weng, Beijing (CN); Caili Zhang, Beijing (CN); Xiaoqian Diao, Beijing (CN); Zhirui Ma, Beijing (CN); Yu Han, Beijing (CN); Wei Luo, Beijing (CN)

(73) Assignee: BEIJING TECHNOLOGY AND BUSINESS UNIVERSITY, Beijing (CN)

( * ) Notice: Subject to any disclaimer, the term of this patent is extended or adjusted under 35 U.S.C. 154(b) by 0 days.

(21) Appl. No.: 18/764,298

(22) Filed: Jul. 4, 2024

(65) Prior Publication Data
US 2024/0409522 A1    Dec. 12, 2024

Related U.S. Application Data

(63) Continuation of application No. PCT/CN2024/073543, filed on Jan. 23, 2024.

(30) Foreign Application Priority Data

Jun. 7, 2023 (CN) .......................... 202310666308.9

(51) Int. Cl.
| | | |
|---|---|---|
| *C07D 301/28* | (2006.01) | |
| *C07D 301/32* | (2006.01) | |
| *C07D 303/44* | (2006.01) | |
| *C08G 63/91* | (2006.01) | |

(52) U.S. Cl.
CPC ......... *C07D 301/28* (2013.01); *C07D 301/32* (2013.01); *C07D 303/44* (2013.01); *C08G 63/916* (2013.01)

(58) Field of Classification Search
CPC .. C07D 301/28; C07D 301/32; C07D 303/44; C08G 63/916
See application file for complete search history.

(56) References Cited

U.S. PATENT DOCUMENTS

2016/0264714 A1    9/2016   Li et al.

FOREIGN PATENT DOCUMENTS

| CN | 102558793 A | 7/2012 |
|---|---|---|
| CN | 102732384 A | 10/2012 |
| CN | 105461871 A | 4/2016 |
| CN | 113845648 A | 12/2021 |
| CN | 113881102 A | 1/2022 |
| CN | 114479398 A | 5/2022 |
| CN | 115058103 A | 9/2022 |
| CN | 116693471 A | 9/2023 |

OTHER PUBLICATIONS

Cai et al. International Journal of Chemical Kinetics, 2018, 50(10), 726-741 (Year: 2018).*
Song et al. J. Applied Poly. Sci. 2021, 138, e50809 (Year: 2021).*
Yang et al. Macromol. Mater. Eng. 2022, 307, 2200364 (Year: 2022).*
Yang Yang et al., "Design and Synthesis of Epoxidized Soybean Oil-Branched Cardanol Ethers as Poly (vinylchloride) Plasticizers," Macromol. Mater. Eng., Date of issue: Aug. 5, 2022, p. 2200364, vol. 307. Related claims: 1-9.
Wei Luo et al., Synergistic Effect of Thermal Stabilization and Plasticization of Epoxidized Cardanol Esters on PVC,: Journal of Polymers and the Environment, Date of issue: Jun. 3, 2023. https://doi.org/10.1007/s10924-023-02933-8 Related claims: 1-9.
Notification to Grant Patent from China Application No. 202310666308.9, mailed Oct. 16, 2023.
First Search Report from China Application No. 202310666308.9, dated Oct. 13, 2023.

* cited by examiner

*Primary Examiner* — Matthew P Coughlin
(74) *Attorney, Agent, or Firm* — Pilloff Passino & Cosenza LLP; Rachel Pilloff; Sean Passino

(57) ABSTRACT

The present disclosure provides a bio-based epoxy chain extender and a preparation method thereof, belonging to the technical field of chain extenders, and the preparation method includes the following steps: (1) mixing ESO and CD and carrying out catalytic reaction to obtain $ESO_n$-CD; and (2) mixing and heating the $ESO_n$-CD with concentrated sulfuric acid, dropwise adding a mixture of glacial acetic acid and hydrogen peroxide for stirring reaction, and after the stirring reaction, carrying out extraction and separation to remove a solvent to obtain the bio-based epoxy chain extender. The present disclosure also provides a bio-based epoxy chain extender prepared by the preparation method.

6 Claims, 10 Drawing Sheets

Mixing ESO and CD and carrying out catalytic reaction to obtain $ESO_n$-CD

↓

Mixing and heating the $ESO_n$-CD with concentrated sulfuric acid, dropwise adding a mixture of glacial acetic acid and hydrogen peroxide for stirring reaction, and after a reaction, carrying out extraction and separation to remove a solvent to obtain the bio-based epoxy chain extender

FIG. 10

BIO-BASED EPOXY CHAIN EXTENDER AND PREPARATION METHOD THEREOF

CROSS-REFERENCE TO RELATED APPLICATIONS

This application is a continuation of PCT/CN2024/073543, filed Jan. 23, 2024 and claims priority of Chinese Patent Application No. 202310666308.9, filed on Jun. 7, 2023, the entire contents of which are incorporated herein by reference.

TECHNICAL FIELD

The present disclosure belongs to the technical field of chain extenders, and in particular to a bio-based epoxy chain extender, a preparation method and an application thereof.

BACKGROUND

Polybutylene succinate (PBS) has excellent biodegradability, melt processability and chemical resistance, as well as good thermal stability and excellent mechanical properties. With the renewability of the synthesized monomers and properties comparable to those of traditional polyolefin plastics, PBS is considered to be a class of biodegradable materials with good prospects for development in the field of packaging films and mulch films. However, there is a major problem limiting the expanded utilization of PBS in the film field, mainly the low barrier properties to oxygen and water vapor, which make PBS incapable of meeting the high barrier requirements in packaging and mulch film applications.

Currently, the problem of poor barrier properties of PBS is addressed by adding a high barrier material, polyglycolic acid (PGA), while compatibilizers/chain extenders are added to improve the compatibility of the two in order to further enhance the phase interfacial adhesion and improve the barrier properties of the material. Since polyester contains terminal carboxyl and terminal hydroxyl groups, the functional groups of chain extenders commonly used in the prior art include epoxy groups, isocyanates, oxazolines, and so on. Epoxy compounds are usually the most used for their efficient chain extension effect, among which BASF's ADR series derived from the copolymerization of styrene and acrylic acid glycidyl ester is the most frequently used. However, ADR chain extenders are unfavorable because of the presence of benzene rings in their structure, the high molecular weight (6,000-7,000 k), the petroleum-based origin of the monomer, and the difficulty of degradation.

Therefore, a technical problem that needs to be solved by the technicians in the field is to provide a chain extender with good capacity-enhancing and chain-extending effect, as well as high stability and synthesis of monomers of biobased origin.

SUMMARY

In order to solve the above technical problems, the present disclosure provides a bio-based epoxy chain extender, a preparation method and an application thereof.

In order to achieve the above objectives, the present disclosure provides the following technical scheme.

A preparation method of a bio-based epoxy chain extender includes the following steps:
(1) mixing epoxidized soybean oil (ESO) and cardanol (CD) and carrying out catalytic reaction to obtain $ESO_n$-CD; and
(2) mixing and heating the $ESO_n$-CD with concentrated sulfuric acid, dropwise adding a mixture of glacial acetic acid and hydrogen peroxide for stirring reaction, and after the stirring reaction, carrying out extraction and separation to remove a solvent to obtain the bio-based epoxy chain extender.

Beneficial effect: the raw material CD in the present disclosure is a multifunctional, renewable and inexpensive organic natural resource derived from cashew nut-shell liquid, an agricultural by-product of the cashew industry, and consists of a mixture of different long-chain phenols. CD contains phenolic hydroxyl groups and double bonds, and reacts with ESO to produce a new $ESO_n$-ECD chain extender. The preparation method is simple in process, cost-effective with high yield, and is convenient for control and large-scale production, while the produced chain extender has good capacity-enhancing effect and strong stability.

Optionally, a molar ratio of the ESO to the CD in step (1) is 3-6:1; and
a catalyst in a process of the catalytic reaction is hydrochloric acid.

Optionally, a temperature of the catalytic reaction in the step (1) is 200 degrees Celsius (° C.) with a reaction duration of 30 minutes (min).

Optionally, an addition ratio of the $ESO_n$-CD, the concentrated sulfuric acid, the glacial acetic acid and the hydrogen peroxide in step (2) is 100 grams (g):2 milliliters (mL):10 mL:20 mL.

Optionally, a mass concentration of the concentrated sulfuric acid is 98%;
a concentration of the glacial acetic acid is 3 equivalents; and
a mass concentration of the hydrogen peroxide is 30%.

Optionally, a temperature for heating in the step (2) is 65° C.; and
a duration for the stirring reaction is 4 hours (h).

A bio-based epoxy chain extender prepared by the preparation method of the bio-based epoxy chain extender.

An application of the bio-based epoxy chain extender in preparation of PBS/PGA composite material.

Optionally, the PBS/PGA composite material includes a PBS/PGA injection molded product or a PBS/PGA composite film.

More optionally, a preparation method of the PBS/PGA composite material includes the following steps:
(1) mixing PBS, PGA and the bio-based epoxy chain extender, and then using a twin-screw to melt, extrude and granulate to obtain a composite master batch, where a temperature of an extruder from a feeding area to a head area is 195-225° C.;
a mass ratio of the PBS to the PGA is 4:1;
an addition amount of the bio-based epoxy chain extender is 0.3-1.0% of a total mass of the PBS and the PGA;
(2) carrying out injection molding to the obtained composite master batch with an injection molding machine to obtain splines, with a processing temperature of 200° C.;
or,
carrying out blow molding to the obtained composite master batch with a blow molding machine to obtain a composite film, and a processing temperature of the blow molding machine is 180-200° C.

The present disclosure provides a bio-based epoxy chain extender and a preparation method thereof. The epoxy chain extender synthesized based on biomass resources in this disclosure has excellent chain extending effect on PBS/PGA composite materials and is capable of synergistically improving the barrier property of the composite film, and also enhancing the interfacial bonding force of the two phases of PBS/PGA, thus improving the mechanical properties of PBS/PGA composite film; moreover, the bio-based epoxy chain extender provided by the present disclosure has excellent compatibilization effect, which not only solves the problem of poor compatibility of the two phases of the biodegradable polyester, but also realizes total degradation, which makes it an alternative to petroleum-based chain extender. Besides, the preparation method provided by the present disclosure requires low raw material cost and has renewable source, which is in line with the requirement of green environment protection, and the process is simple and does not pollute the environment, indicating a good substitute for petroleum-based chain extender.

BRIEF DESCRIPTION OF THE DRAWINGS

The accompanying drawings, which constitute a part of this application, are used to provide a further understanding of this application. The illustrative embodiments of this application and their descriptions are used to explain this application, and do not constitute an improper limitation of this application. In the attached drawings:

FIG. 10 shows a process illustrating the preparation method of the bio-based epoxy chain extender.

DETAILED DESCRIPTION OF THE EMBODIMENTS

Figure 1:
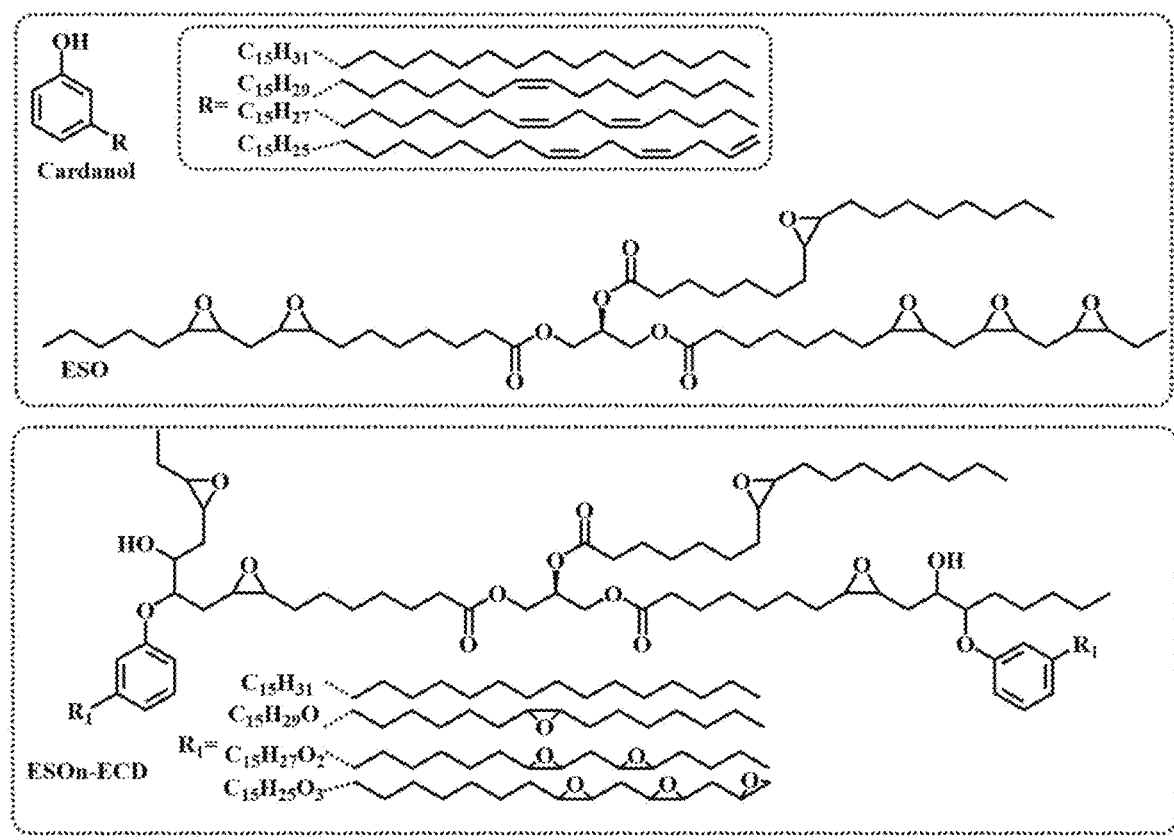
FIG. 1 shows schematic diagrams of the structural formulas of the reactants ESO and CD, and the product $ESO_n$-ECD in Embodiments 1 and 2.

In the following, the technical schemes in the embodiments of the present disclosure are clearly and completely described with reference to the attached drawings. Obviously, the described embodiments are only a part of the embodiments of the present disclosure, but not the whole embodiments. Based on the embodiments in the present disclosure, all other embodiments obtained by ordinary technicians in the field without creative labor belong to the scope of protection of the present disclosure.

In order to make the above objectives, features and advantages of the present disclosure more obvious and easy to understand, the present disclosure will be further described in detail with the attached drawings and specific embodiments.

Some sources of raw materials used in the embodiments of the present disclosure are as follows:

CD (cardanol): Dining Huakai Resin Biochemical Co., Ltd. of Shandong, China;

ESO (epoxidized soybean oil): Macklin Co., Ltd. of Shanghai, China;

ADR4468: BASF;

PBS (polybutylene succinate): Showa Denko, Japan, with mark of 1001MD;

PGA (polyglycolic acid, high barrier material): Shanghai Pujing Chemical Technology Co., Ltd.

The present disclosure provides a preparation method of a bio-based epoxy chain extender, including the following steps as shown in FIG. 10:

(1) mixing epoxidized soybean oil (ESO) and cardanol (CD) and carrying out catalytic reaction to obtain $ESO_n$-CD; and (2) mixing and heating the $ESO_n$-CD with concentrated sulfuric acid, dropwise adding a mixture of glacial acetic acid and hydrogen peroxide for stirring reaction, and after the stirring reaction, carrying out extraction and separation to remove a solvent to obtain the bio-based epoxy chain extender.

Embodiment 1

The preparation method of the bio-based epoxy chain extender, including the following steps:

(1) mixing ESO and CD in a molar ratio of 3:1 in a three-necked flask equipped with a magnetic stirrer, adding a drop of concentrated hydrochloric acid as a catalyst, and then reacting at a constant temperature of 200° C. for 30 min to obtain the product $ESO_3$-CD; and (2) mixing 100 g of $ESO_3$-ECD with 2 mL of $H_2SO_4$ (98 wt. %) and heating to 65° C., then dropwise adding a mixture of 10 mL of glacial acetic acid (3 equivalents) and 20 mL of $H_2O_2$ (30 wt. %), and then magnetically stirring the mixed solution for 4 h at 65° C.; after reaction, extracting and separating the product from the organic phase in dichloromethane, and then removing the organic phase by rotary evaporation to obtain the bio-based epoxy chain extender $ESO_3$-ECD.

The yield of the obtained bio-based epoxy chain extender $ESO_3$-ECD is 90% and the epoxy value is 6.62%.

Embodiment 2

The preparation method of the bio-based epoxy chain extender, including the following steps:

(1) mixing ESO and CD in a molar ratio of 6:1 in a three-necked flask equipped with a magnetic stirrer, adding a drop of concentrated hydrochloric acid as a catalyst, and then reacting at a constant temperature of 200° C. for 30 min to obtain the product $ESO_6$-CD; and (2) mixing 100 g of $ESO_6$-ECD with 2 mL of $H_2SO_4$ (98 wt. %) and heating to 65° C., then dropwise adding a mixture of 10 mL of glacial acetic acid (3 equivalents) and 20 mL of $H_2O_2$ (30 wt. %), and then magnetically stirring the mixed solution for 4 h at 65° C.; after reaction, extracting and separating the product from the organic phase in dichloromethane, and then removing the organic phase by rotary evaporation to obtain the bio-based epoxy chain extender $ESO_6$-ECD.

The yield of the obtained bio-based epoxy chain extender $ESO_6$-ECD is 92% and the epoxy value is 4.78%.

Figure 2:
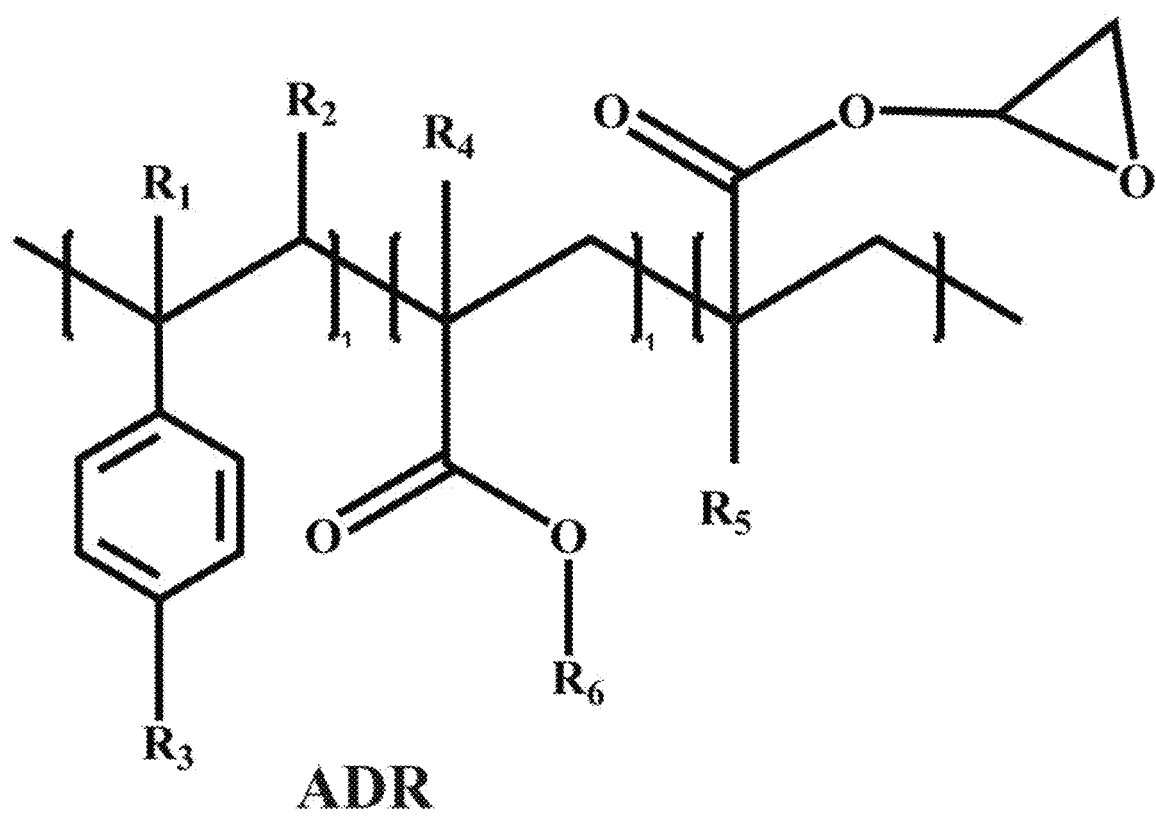
FIG. 2 shows the structural formula of BASF ADR4468.
Figure 3:
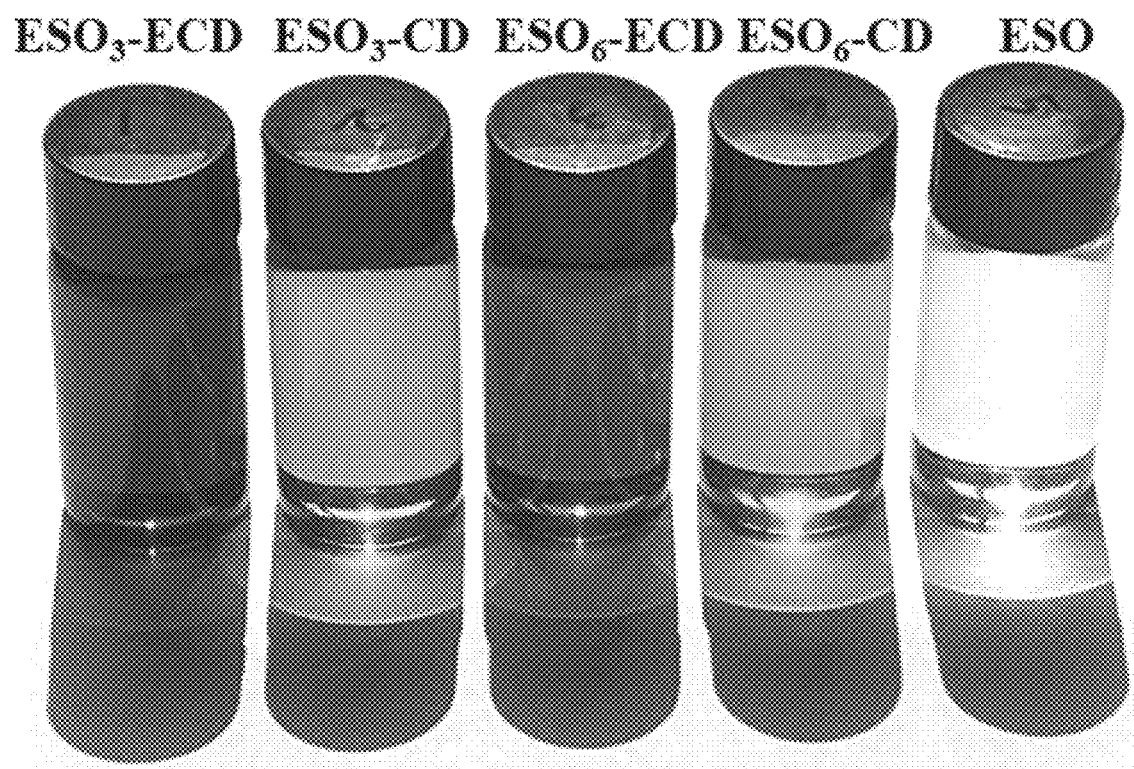
FIG. 3 is a photograph showing $ESO_n$-CD, $ESO_n$-ECD and ESO obtained in Embodiments 1 and 2.

The structural formulas of the reactants ESO and CD used in Embodiments 1-2 and the products $ESO_n$-ECD are shown in FIG. 1. The chemical structures of the ADR4468 is shown in FIG. 2; and the pictures of the two chain extenders $ESO_3$-ECD and $ESO_6$-ECD prepared in Embodiments 1-2 as well as $ESO_3$-CD, $ESO_6$-CD and ESO synthesized in the step (1) are shown in FIG. 3. By comparison, it is observed that the color of $ESO_n$-ECD obtained in step (2) is deeper than that of $ESO_n$-CD, indicating the successful occurrence of oxidation reaction.

Embodiment 3

The preparation method of the PBS/PGA composite material includes the following steps:
mixing PBS, PGA and the bio-based epoxy chain extender obtained in Embodiment 1, and then melting, extruding and granulating with a twin screw to obtain composite master batch, where the temperature of the extruder from the feeding area to the head area is 195-225° C.; among them, the mass ratio of PBS to PGA is 4:1, and the addition amount of the bio-based epoxy chain extender obtained in Embodiment 1 is 0.3% of the total mass of PBS and PGA; then, carrying out injection molding to the composite master batch at 200° C. by using an injection molding machine to obtain PBS/PGA composite spline.

Embodiments 4-6

The preparation method of PBS/PGA composite material is different from Embodiment 3 in that the addition amount of bio-based epoxy chain extender obtained in Embodiment 1 is 0.5%, 0.7% and 1.0% of the total mass of PBS and PGA in turn.

Embodiment 7

The preparation method of the PBS/PGA composite material includes the following steps:
mixing PBS, PGA and the bio-based epoxy chain extender obtained in Embodiment 2, and then melting, extruding and granulating with a twin screw to obtain composite master batch, where the temperature of the extruder from the feeding area to the die area is 195-225° C.; among them, the mass ratio of PBS to PGA is 4:1, and the bio-based epoxy chain extender obtained in Embodiment 1 accounts for 0.3% of the total mass of PBS and PGA; then, carrying out injection molding to the composite master batch at 200° C. by using an injection molding machine to obtain PBS/PGA composite spline.

Embodiments 8-10

The preparation method of the PBS/PGA composite material is different from Embodiment 7 in that the bio-based epoxy chain extender obtained in Embodiment 2 accounts for 0.5%, 0.7% and 1.0% of the total mass of PBS and PGA in turn.

Comparative Embodiment 1

The preparation method of PBS/PGA composite material is different from Embodiment 3 in that the bio-based epoxy chain extender obtained in Embodiment 1 is not added.

Comparative Embodiment 2

The preparation method of the PBS/PGA composite material includes the following steps:
mixing PBS, PGA and BASF ADR4468, and then melting, extruding and granulating with a twin screw to obtain composite master batch, where the temperature of the extruder from the feeding area to the head area is 195-225° C.; among them, the mass ratio of PBS and PGA is 4:1, and the amount of ADR4468 is 0.3% of the total mass of PBS and PGA; then, carrying out injection molding to the composite master batch at 200° C. by using an injection molding machine to obtain PBS/PGA composite spline.

Comparative Embodiments 3-5

The preparation method of the PBS/PGA composite material is different from Embodiment 7 in that the addition amount of BASF ADR4468 is 0.5%, 0.7% and 1.0% of the total mass of PBS and PGA in turn.

Embodiment 11

The preparation method of the PBS/PGA composite film includes the following steps:
mixing PBS, PGA and the bio-based epoxy chain extender obtained in Embodiment 1, and then melting, extruding and granulating with a twin screw to obtain composite master batch, where the temperature of the extruder from the feeding area to the head area is 195-225° C.; among them, the mass ratio of PBS to PGA is 4:1, and the bio-based epoxy chain extender obtained in Embodiment 1 accounts for 0.7% of the total mass of PBS and PGA; then, carrying out blow-molding to the composite master batch by a blow molding machine at 180-200° C. to obtain the PBS/PGA composite film.

Embodiment 12

The preparation method of PBS/PGA composite film is different from Embodiment 11 in that the bio-based epoxy chain extender obtained in Embodiment 2 is used.

Comparative Embodiment 6

The preparation method of PBS/PGA composite film is different from Embodiment 11 in that no chain extender is used.

Comparative Embodiment 7

The preparation method of PBS/PGA composite film is different from Embodiment 11 in that BASF ADR4468 is used instead of the bio-based epoxy chain extender obtained in Embodiment 1.

Technical Effects

1. The products prepared in each embodiment are characterized by the following methods.

(1)

Proton nuclear magnetic resonance ($^1$H NMR) spectroscopy is performed on a Broker Avance 400 instrument with a frequency of 400 MHz, using $CDCl_3$ as the solvent.

The thermal stability of each bio-based epoxy chain extender is measured by thermogravimetric analysis (TGA) in STA7200 (Hitachi, Japan). Specifically, under the condition of nitrogen purging, the heating rate is 20° C./min, and the measuring temperature range is 40-500° C. The weight loss rate of each chain extender with the increase of temperature is recorded.

(2) On the electronic universal testing machine controlled by microcomputer (CMT6104, China), the mechanical properties of injection-molded splines and films are tested according to GB/T1040.1-2006, and the elongation at break (EB, %) and tensile strength (TS, MPa) of the samples are obtained. Among them, the spacing between fixtures is set to 50 mm, the stretching speed is 50 mm/min, and each group of samples is tested for 5-10 times. The average value and the error are calculated.

Using the same machine, the tear resistance of the film is tested according to the standard of GB/T106578.1-2008. During the test, the distance between fixtures is set to 50 mm, and the tearing rate is 200 mm/min. Each group of samples is tested for 5 times, and the average value is taken according to the effective value.

(3) Under the condition of JSM-6700F voltage of 10 kV, the microstructure of the sample is analyzed by scanning electron microscope (SEM). Each group of samples is soaked in liquid nitrogen for 15 min, and a thin gold layer is coated on the fracture surface to improve the conductivity of the samples.

(4) According to ASTM D3985, the $O_2$ permeability of PBS/PGA composite film is measured by VAC-V2 differential pressure gas permeameter at 23° C. and 30% relative humidity.

According to GB/T1037, at 38° C. and 90% relative humidity, the water vapor permeability of PBS/PGA composite film is measured by C360M weight loss method with a water vapor permeameter.

Figure 4:
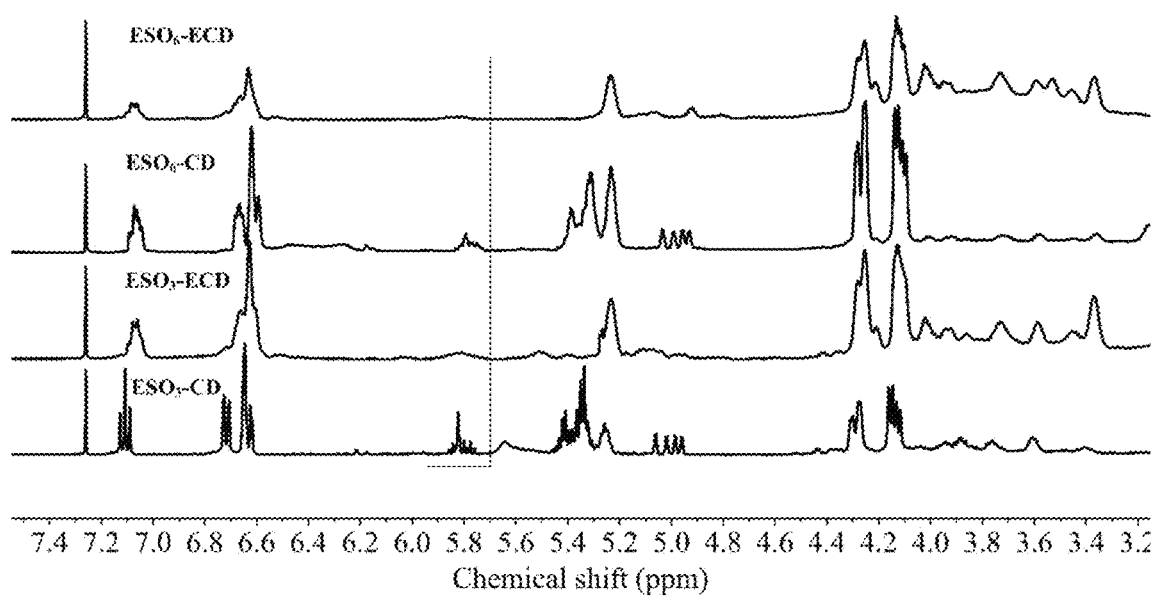
FIG. 4 is the NMR spectra of $ESO_n$-CD and $ESO_n$-ECD obtained in Embodiments 1 and 2.

2. The characterization results and analysis are as follows:

FIG. 4 shows the $^1$HNMR spectra of the bio-based epoxy chain extenders obtained in Embodiments 1 and 2.

By comparing the $^1$HNMR spectra, it is found that after the oxidation reaction in step (2), the signal peaks of $ESO_n$-ECD at 5.75 ppm and 5.0 ppm are obviously reduced compared with $ESO_n$-CD, indicating that the double bond disappears and the epoxidation reaction occurs.

Figure 5:
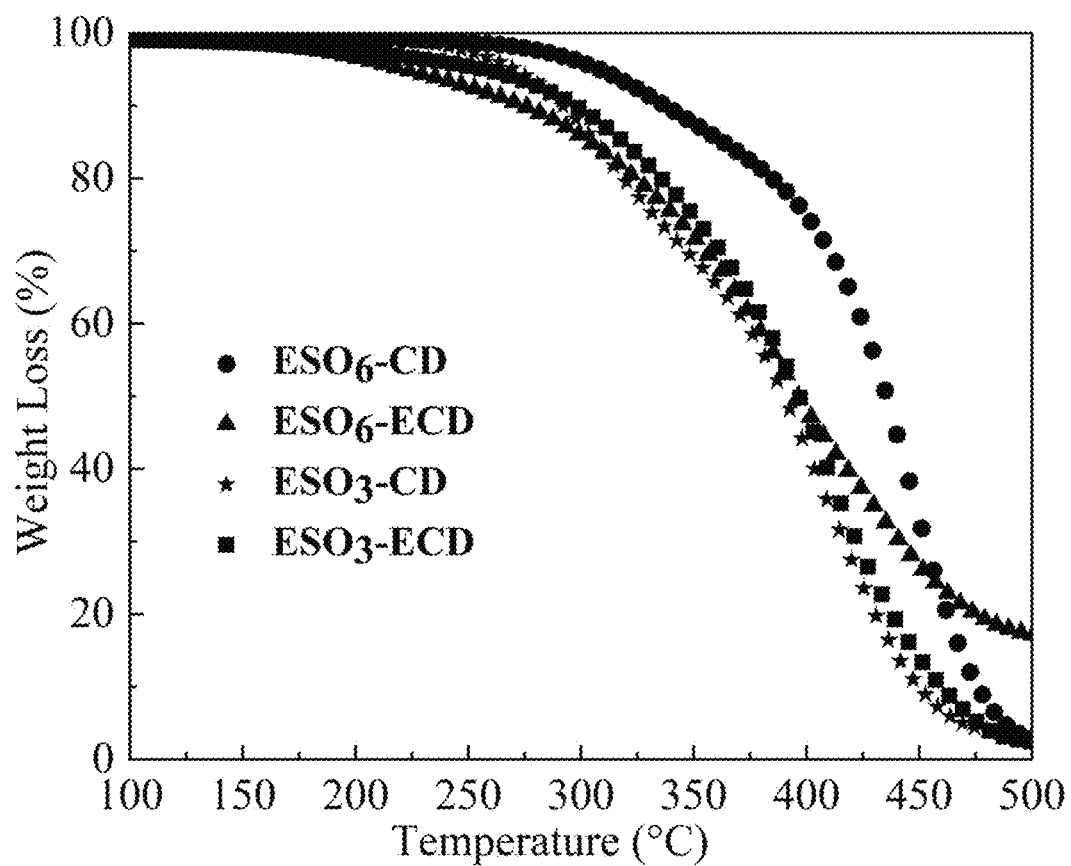
FIG. 5 illustrates the thermogravimetric curves of $ESO_n$-CD and $ESO_n$-ECD obtained in Embodiments 1 and 2.

FIG. 5 shows the thermogravimetric curves of the bio-based epoxy chain extenders obtained in Embodiments 1 and 2, as shown in Table 3. The thermal stability of the synthesized chain extenders is evaluated by TGA. By comparing the weight loss temperature of 5% of the chain extender ($T_{d-5}$%), it is found that the thermal stability of $ESO_n$-ECD is reduced compared to $ESO_n$-CD, and the thermal stability of $ESO_3$-ECD is better than that of $ESO_6$-ECD.

TABLE 3

Thermal decomposition temperature of chain extender

| Samples | $T_{d-5}$%(° C.) | $T_{d-10}$% (° C.) |
|---|---|---|
| ESO | 328.6 | 364.5 |
| $ESO_3$-CD | 270.3 | 291.4 |
| $ESO_3$-ECD | 256.4 | 296.7 |
| $ESO_6$-CD | 342.8 | 315.7 |
| $ESO_6$-ECD | 218.7 | 273.8 |

The mechanical properties of composite injection-molded splines obtained in Embodiments 3-10 and Comparative embodiments 1-5 are tested, and their tensile properties and impact properties are shown in Table 4, and the compatibilization effects of different chain extenders are studied correspondingly. It is observed from Table 4 that the addition of ADR or $ESO_n$-ECD may improve the tensile strength and elongation at break of the composite material compared with the compatibilized blends, which proves that the addition of chain extender is capable of enhancing the interfacial bonding force. The epoxy group in the chain extender reacts with carboxyl and/or hydroxyl groups of PBS and PGA, thus promoting effective immobilization between phases. With the content of chain extender increasing from 0.3% to 0.7%, the tensile strength, elongation at break, tensile modulus and impact strength of the composite material are all increased. However, when the content of chain extender continues to increase to 1.0%, the mechanical properties will decrease, which is mainly caused by excessive chain extender. The excessive chain extender fails to react with the terminal carboxyl group of PBS and PGA, and it plays a plasticizing role in the composite, which will lead to the decrease of mechanical properties.

It may be further observed from Table 4 that the component with 0.7% chain extender in the composite material has the best mechanical properties, among which $ESO_n$-ECD shows a better value than ADR, which may be due to its lower viscosity, as $ESO_n$-ECD is an oily liquid with a molecular weight of about 1,000, while ADR is in a solid powder state with a molecular weight of about 6,000-7,000. Generally, during melt mixing, the components with lower viscosity in the blend tend to encapsulate other components. Therefore, $ESO_n$-ECD should be easier to migrate to the phase interface between PGA and PBS, thus serving as a bridge between the two phases. In addition, the addition of $ESO_n$-ECD also promotes the significant increase of impact strength, which further proves the enhancement of two-phase interface. From the mechanical properties, it is observed the chain extension and compatibilization effect of $ESO_3$-ECD is better than $ESO_6$-ECD. This is related to the number of epoxy groups, which increases as the proportion of cardanol increases in $ESO_n$-ECD, and a higher number of epoxy groups favours a higher efficiency of the reaction and accelerates the chain extension reaction.

TABLE 4

Tensile and impact properties of PBS/PGA injection moulded samples

| Samples | Tensile strength (MPa) | Elongation at break (%) | Tensile modulus (MPa) | Notched impact strength (KJ/m$^2$) |
|---|---|---|---|---|
| Comparative embodiment 1 | 15.3 ± 1.8 | 205.7 ± 5.6 | 180.4 ± 3.1 | 30.7 ± 2.3 |
| Comparative embodiment 2 | 16.54 ± 2.34 | 248.12 ± 82.72 | 161.45 ± 47.11 | 34.35 ± 3.31 |
| Comparative embodiment 3 | 17.08 ± 1.12 | 295.83 ± 63.23 | 148.93 ± 11.48 | 37.54 ± 2.44 |
| Comparative embodiment 4 | 19.58 ± 3.33 | 348.98 ± 57.94 | 153.67 ± 67.36 | 43.36 ± 3.91 |
| Comparative embodiment 5 | 18.36 ± 1.67 | 321.95 ± 33.54 | 119.73 ± 13.72 | 30.64 ± 2.62 |
| Embodiment 3 | 19.15 ± 2.12 | 393.58 ± 43.45 | 134.92 ± 61.19 | 34.44 ± 2.12 |
| Embodiment 4 | 19.62 ± 2.55 | 401.68 ± 50.94 | 159.38 ± 95.36 | 42.09 ± 2.23 |
| Embodiment 5 | 19.44 ± 3.14 | 410.38 ± 63.45 | 165.83 ± 32.03 | 45.59 ± 3.69 |
| Embodiment 6 | 18.75 ± 2.65 | 334.76 ± 79.47 | 128.63 ± 48.34 | 43.11 ± 4.73 |
| Embodiment 7 | 18.68 ± 1.87 | 388.78 ± 95.43 | 153.33 ± 57.64 | 40.37 ± 1.31 |
| Embodiment 8 | 18.85 ± 2.39 | 394.55 ± 70.23 | 147.95 ± 29.84 | 41.75 ± 2.09 |
| Embodiment 9 | 19.38 ± 1.27 | 409.23 ± 52.89 | 155.27 ± 68.82 | 43.95 ± 3.44 |
| Embodiment 10 | 19.48 ± 0.96 | 396.47 ± 38.03 | 133.62 ± 19.72 | 42.32 ± 2.84 |

Figure 6:
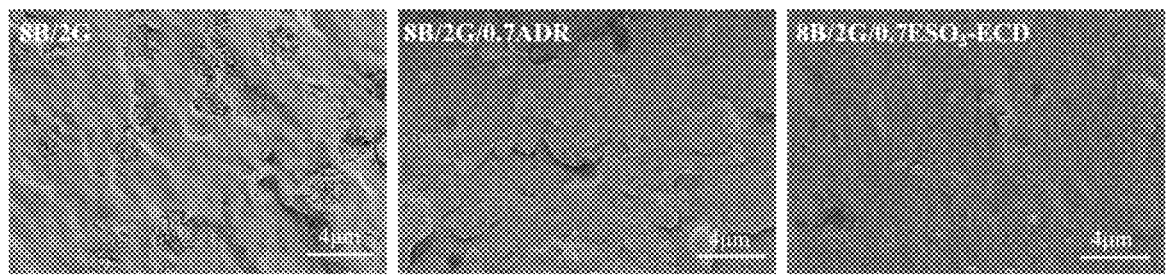
FIG. 6 shows SEM images of sections of PBS/PGA injection molded samples obtained from Embodiment 5, Comparative embodiment 1 and Comparative embodiment 4.

FIG. 6 shows SEM images of injection spline sections of the composite materials obtained from Embodiment 5, Comparative embodiment 1 and Comparative embodiment 4, providing the micro-morphology about the compatibilization of PBS/PGA blends. It may be seen that the injection spline section obtained in Comparative embodiment 1 presents a typical sea-island morphology, and PGA is mainly dispersed in PBS matrix in granular form, and obvious phase interface is observed.

After adding 0.7% ADR or ESO$_3$-ECD in Comparative embodiment 4 and Embodiment 5, the phase interface is decreased. The composite injection-molded spline obtained in Embodiment 5 shows a small and well-adhered PGA dispersed phase, in addition to improved compatibility and better interface adhesion.

Figure 7:
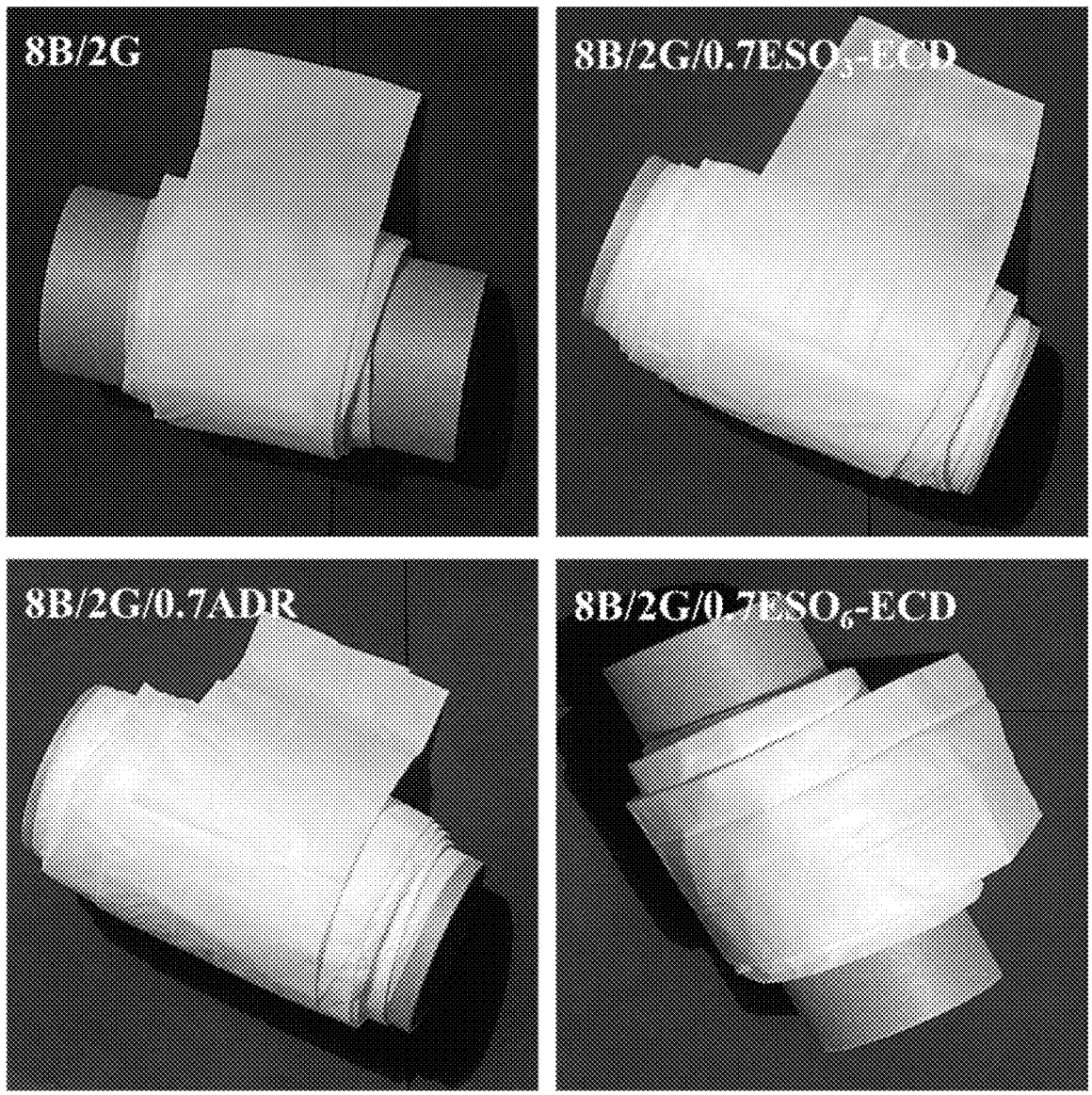
FIG. 7 shows physical diagrams of PBS/PGA composite films obtained in Embodiments 11-12 and Comparative embodiments 6-7.

The composite films obtained in Embodiments 11-12 and Comparative embodiments 6-7 are shown in FIG. 7. From the appearance and morphology of the composite film, it is observed that the composite film with ESO$_3$-ECD chain extender obtained in Embodiment 1 has a smoother membrane surface, in addition, the film bubbles are larger and the stability is good during production and processing.

Tables 5 and 6 show the mechanical properties of PBS/PGA composite films obtained in Comparative embodiments 6-7 and Embodiments 11-12. As shown in the results, the tensile and tear properties of the composite films obtained in Embodiment 11 are the best.

TABLE 5

Tensile properties of PBS/PGA composite film

| | Tensile strength (MPa) | | Elongation at break (%) | |
|---|---|---|---|---|
| Samples | MD | TD | MD | TD |
| Comparative embodiment 6 | 9.52 ± 0.82 | 4.34 ± 0.39 | 374.01 ± 68.48 | 58.33 ± 5.71 |
| Comparative embodiment 7 | 9.98 ± 1.03 | 8.39 ± 0.61 | 377.71 ± 76.41 | 153.72 ± 23.03 |
| Embodiment 11 | 12.27 ± 1.42 | 7.25 ± 1.68 | 401.99 ± 49.35 | 179.84 ± 45.22 |
| Embodiment 12 | 9.05 ± 1.01 | 5.12 ± 1.03 | 270.36 ± 60.27 | 53.97 ± 14.31 |

TABLE 6

Tearing properties of PS/PGA composite film

| | Tensile strength (MPa) | | Elongation at break (%) | |
|---|---|---|---|---|
| Samples | MD | TD | MD | TD |
| Comparative embodiment 6 | 9.52 ± 0.82 | 4.34 ± 0.39 | 374.01 ± 68.48 | 58.33 ± 5.71 |
| Comparative embodiment 7 | 9.98 ± 1.03 | 8.39 ± 0.61 | 377.71 ± 76.41 | 153.72 ± 23.03 |
| Embodiment 11 | 12.27 ± 1.42 | 7.25 ± 1.68 | 401.99 ± 49.35 | 179.84 ± 45.22 |
| Embodiment 12 | 9.05 ± 1.01 | 5.12 ± 1.03 | 270.36 ± 60.27 | 53.97 ± 14.31 |

Figure 8:
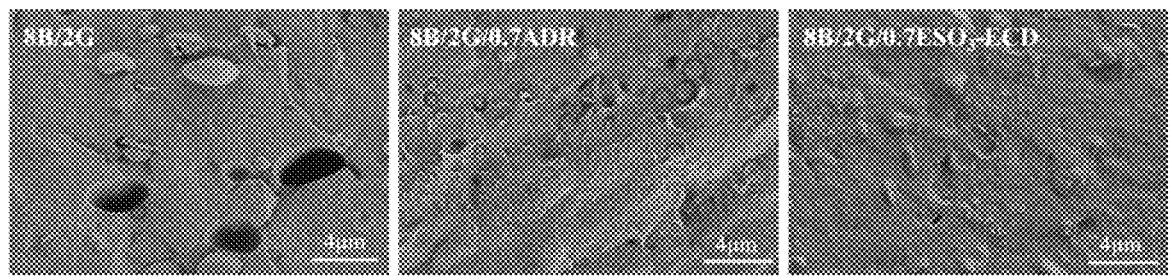
FIG. 8 shows SEM images of the longitudinal section (MD direction) of the PBS/PGA composite films obtained from Embodiment 11 and Comparative embodiments 6-7.
Figure 9:
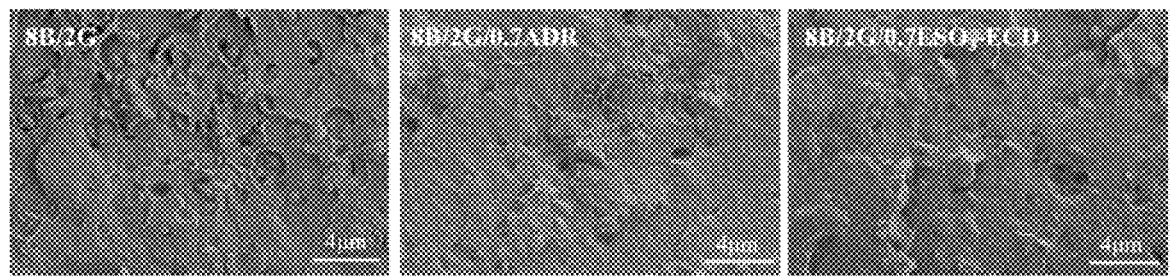
FIG. 9 shows SEM images of the longitudinal section (TD direction) of the PBS/PGA composite films obtained from Embodiment 11 and Comparative embodiments 6-7.

FIG. 8 and FIG. 9 are SEM images of longitudinal and transverse sections of PBS/PGA composite films obtained in Comparative embodiments 6-7 and Embodiment 11, respectively. The composite film obtained in Comparative embodiment 6 without compatibilization modification is similar to the results obtained from the SEM section of injection-molded spline, and PGA is dispersed in the PBS matrix in particles. Due to the weak bonding force between phase interfaces, rigid PGA particles will be pulled out from the flexible PBS matrix during the brittle fracture of the sample, thus leaving holes in the cross section of the composite film obtained in Comparative embodiment 6. However, in Embodiment 11, after adding 0.7% $ESO_3$-ECD, the two-phase interface in the composite film is obviously reduced, and the transverse and longitudinal sections become smooth, which further explains the good compatibilization effect of $ESO_3$-ECD.

In addition, as shown in Table 7, the composite film obtained in Embodiment 11 exhibits the lowest oxygen and water vapour permeability and has good barrier properties due to the reduction of the phase interfaces as compared to the unmodified composite film obtained in Comparative embodiment 6.

TABLE 7

PBS/PGA composite film oxygen and water vapor permeability

| Samples | Oxygen permeability ($cm^3/m^2 \cdot 24$ h) | Water vapour permeability $g/(m^2 \cdot day)$ |
|---|---|---|
| Comparative embodiment 6 | 0.082 | 287 |
| Comparative embodiment 7 | 0.063 | 238 |
| Embodiment 11 | 0.014 | 202 |
| Embodiment 12 | 0.045 | 267 |

According to the present disclosure, a bio-based epoxidized compound is prepared from biological cardanol and epoxidized soybean oil as raw materials, and is used as an active compatibilizer/chain extender additive of a PBS/PGA (80:20 wt %) blend, and meanwhile, the effectiveness of the bio-based compound is compared with the petroleum-derived glycidyl ester-based copolymer ADR4468 widely used in the prior art. The results show that compared with unmodified PBS/PGA incompatible blends, adding 0.7 part of $ESO_3$-ECD may effectively improve the mechanical properties of composite material/films. It may be clearly seen from SEM that the addition of $ESO_3$-ECD is capable of strengthening the phase interface of the two phases and plays a bridging role. To sum up, $ESO_3$-ECD has excellent effect on toughening chain-extended PBS/PGA blends.

The chain extender prepared by the present disclosure is obtained from monomers of biomass origin, which is green and non-toxic, and is also a good substitute for petroleum-based chain extender. It may be directly applied in the field of food packaging, and the bio-based chain extender solves the problem of poor barrier properties of biodegradable films, as well as makes a positive significance for broadening the application field of PBS.

The above describes only the preferred embodiments of this application, but the protection scope of this application is not limited to this. Any change or replacement that may be easily thought of by a person familiar with this technical field within the technical scope disclosed in this application should be included in the protection scope of this application. Therefore, the protection scope of this application should be based on the protection scope of the claims.

What is claimed is:

1. A preparation method of a bio-based epoxy chain extender, comprising following steps:
    (1) mixing ESO and CD and carrying out catalytic reaction to obtain $ESO_n$-CD; and
    (2) mixing and heating the $ESO_n$-CD with concentrated sulfuric acid, dropwise adding a mixture of glacial acetic acid and hydrogen peroxide for stirring reaction, and after a reaction, carrying out extraction and separation to remove a solvent to obtain the bio-based epoxy chain extender;
    wherein the ESO is epoxidized soybean oil; and
    the CD is cardanol.

2. The preparation method of the bio-based epoxy chain extender according to claim 1, wherein a molar ratio of the ESO to the CD in step (1) is 3-6:1; and
    a catalyst in a process of the catalytic reaction is hydrochloric acid.

3. The preparation method of the bio-based epoxy chain extender according to claim 1, wherein a temperature of the catalytic reaction in the step (1) is 200° C. and a reaction duration is 30 min.

4. The preparation method of the bio-based epoxy chain extender according to claim 1, wherein an addition ratio of the $ESO_n$-CD, the concentrated sulfuric acid, the glacial acetic acid and the hydrogen peroxide in step (2) is 100 g:2 mL:10 mL:20 mL.

5. The preparation method of the bio-based epoxy chain extender according to claim 4, wherein a mass concentration of the concentrated sulfuric acid is 98%;
    an amount of the glacial acetic acid is 3 molar equivalents; and
    a mass concentration of the hydrogen peroxide is 30%.

6. The preparation method of the bio-based epoxy chain extender according to claim 1, wherein a heating temperature in step (2) is 65° C.; and
    a duration of the stirring reaction is 4 h.

* * * * *